US00PP21757P2

(12) United States Plant Patent
Caton

(10) Patent No.: US PP21,757 P2
(45) Date of Patent: Mar. 1, 2011

(54) ***HAKONECHLOA* PLANT NAMED 'FUBUKI'**
(50) Latin Name: *Hakonechloa macra*
Varietal Denomination: Fubuki

(75) Inventor: Lynne Allene Caton, Olympia, WA (US)

(73) Assignee: Briggs Nursery, LLC, Porter, WA (US)

( * ) Notice: Subject to any disclaimer, the term of this patent is extended or adjusted under 35 U.S.C. 154(b) by 0 days.

(21) Appl. No.: 12/653,030

(22) Filed: Dec. 7, 2009

(51) Int. Cl.
*A01H 5/00* (2006.01)

(52) U.S. Cl. ..... Plt./384
(58) Field of Classification Search ..... Plt./384

See application file for complete search history.

*Primary Examiner*—Annette H Para
(74) *Attorney, Agent, or Firm*—Jondle & Associates, P.C.

(57) ABSTRACT

A *Hakonechloa* variety particularly distinguished by unique white and green striped foliage and a small and compact growth habit when compared to other varieties of the species, is disclosed.

1 Drawing Sheet

Genus and species: *Hakonechloa macra.*
Variety denomination: 'Fubuki'.

BACKGROUND OF THE NEW PLANT

The present invention comprises a new and distinct variety of *Hakonechloa,* botanically known as *Hakonechloa macra,* a variety of the Japanese forest grass, and hereinafter referred to by the variety name 'Fubuki'. The new variety originated from a whole plant mutation of the *Hakonechloa macra* parent 'Aureola' (unpatented) in a nursery in Porter, Wash. in September 2008.

The new variety was first propagated in September 2008, and has been asexually reproduced repeatedly by in vitro propagation for at least nine generations in Porter, Wash. The present invention has been found to retain its distinctive characteristics through successive asexual propagations by in vitro propagation.

'Fubuki' has not been made publicly available or sold more than one year prior to filing of this application.

SUMMARY OF THE INVENTION

The following are the most outstanding and distinguishing characteristics of the new variety when grown under normal horticultural practices in Porter, Wash.

1. Unique white and green striped foliage; and
2. A small and compact growth habit when compared to other varieties of the species.

DESCRIPTION OF THE PHOTOGRAPHS

This new *Hakonechloa* plant is illustrated by the accompanying photographs which show overall plant habit and foliage of the plant. The colors shown are as true as can be reasonably obtained by conventional photographic procedures. The photos are of 9-month-old plants grown outdoors in a poly-covered greenhouse with a 50% shade cloth in 10.0 cm containers in Porter, Wash. in late summer/early autumn.

DESCRIPTION OF THE NEW VARIETY

Figure 1:
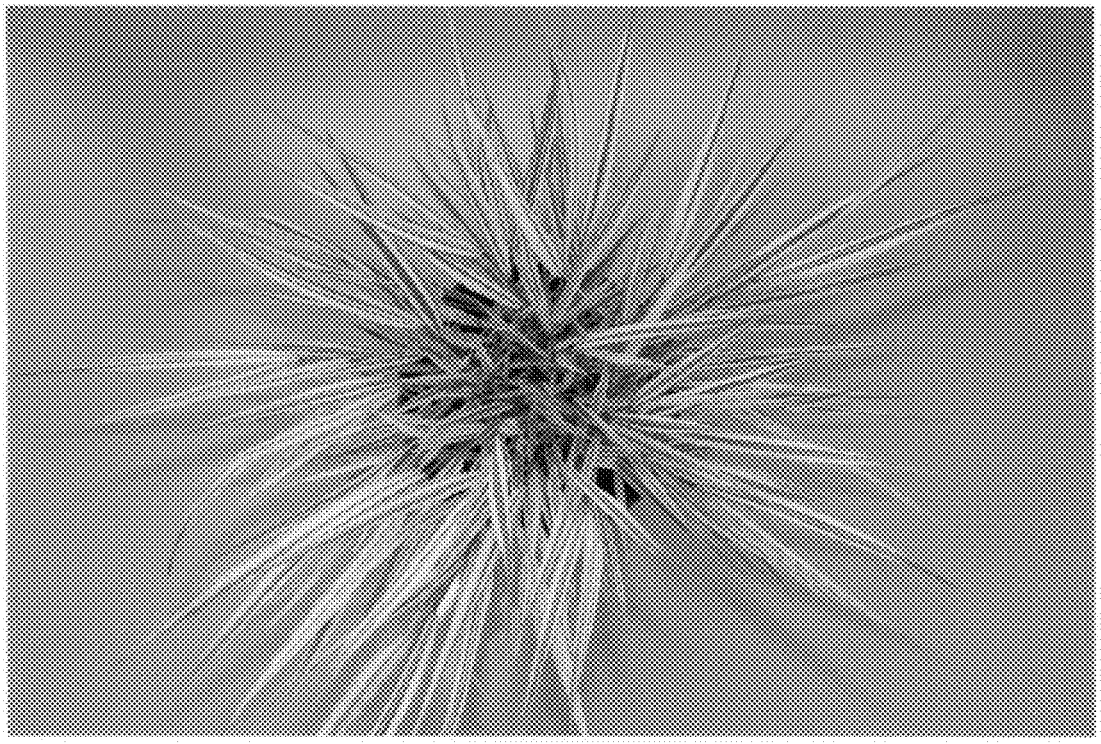
FIG. 1 shows a view of the foliage from above the plant.
Figure 2:
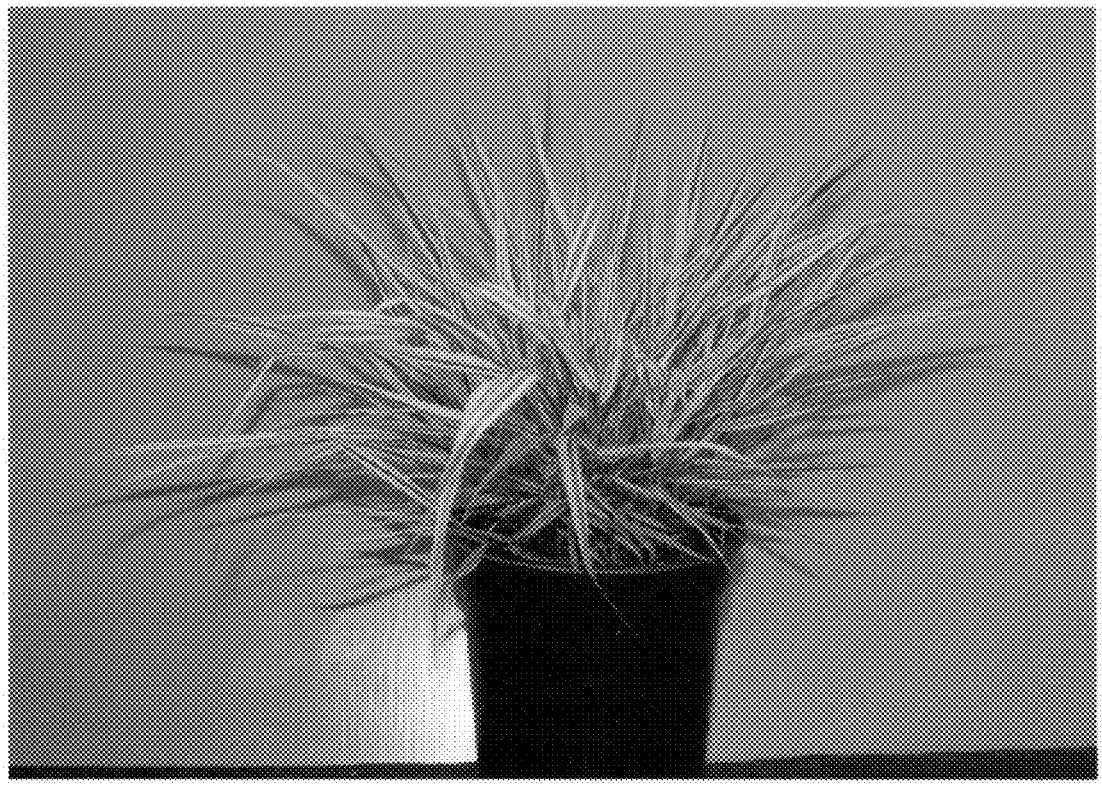
FIG. 2 shows the whole plant, including the foliage and habit.

The following detailed descriptions set forth the distinctive characteristics of 'Fubuki'. The data which define these characteristics were collected from asexual reproductions carried out in Porter, Wash. The plant history was taken on 9-month-old plants grown in 10.0 cm containers outdoors in a poly-covered greenhouse with 50% shade cloth in late summer/early autumn. Color references were taken under natural light and are to The R.H.S. Colour Chart of The Royal Horticultural Society of London (R.H.S.) (1995).

DESCRIPTION OF THE NEW PLANT

Classification:
- *Family.*—Poaceae.
- *Botanical name.*—*Hakonechloa macra.*
- *Common name.*—Japanese forest grass.
- *Variety name.*—'Fubuki'.

General description:
- *Blooming habit.*—Late summer.
- *Plant habit.*—Compact mound, more upright and spiky than other forms of the same species.
- *Plant height.*—28.0 cm.
- *Plant width (spread).*—40.0 cm.
- *Hardiness.*—At least to USDA zone 5.
- *Root description.*—Fibrous, hairy white roots.

Growth and propagation:
- *Propagation type.*—Tissue culture (clonal micropropagation), or division.
- *Vigor.*—Relatively slow grower (typical to the species).

Culm (stem) description:
- *Number per plant.*—68 culms per plant.
- *Branching habit.*—Multiple culms emerge from the crown of the plant.
- *Color.*—Culm color is RHS 154D (Yellow-green), but most of the culm is covered by leaf sheaths that are RHS 185D (Greyed-purple).
- *Length.*—Culm length is 16.0 cm from crown to uppermost node; uppermost leaf adds 12.0 cm, for a total visual length of 28.0 cm.
- *Width.*—Culm width is 0.2 cm.
- *Surface texture.*—Smooth (not pubescent).

*Internode length.*—Internodes are 2.0 cm apart on the basal portion of the culm, shortening to 1.0 cm towards the expanding tip of the culm.

Foliage (leaf) description:

*Number* (*per stem*).—10 leaves per 16.0 cm culm, 7 leaves per 11.0 cm culm.

*Arrangement.*—Leaves are arranged in an alternate pattern on opposite sides of the culm.

*Leaf attachment.*—Leaves are attached to culm by a sheath; sheath is most typically 2.0 cm long, except at the expanding tip of the culm where it can be 1.0 cm long.

*Color.*—Leaves have bi-colored striation, dark-green and creamy-white multiple stripes per leaf, most often with a dark-green margin, but occasionally a creamy-white margin. Upper and lower surfaces: RHS 139A (Dark-green) stripes interspersed with RHS 155A (White) stripes. The number of stripes can vary; a typical leaf has 8 dark-green stripes with 7 white stripes. Young emerging leaves start with RHS 139A (Green) stripes with RHS 160C (Greyed-yellow) stripes and once the leaves are fully expanded and mature the RHS 160C color fades to RHS 155A (White).

*Shape.*—Linear (long and very narrow).

*Apex.*—Acuminate (long tapering).

*Base.*—Cuneate.

*Margin.*—Entire.

*Surface texture.*—Smooth.

*Length.*—11.0 cm leaf blade with 3.0 cm sheath at base of leaf (total length is 14.0 cm).

*Width.*—0.8 cm at the widest point.

*Pubescence.*—Visibly absent but under a 10X lens there are short hairs apparent.

*Venation type.*—Central midrib, parallel venation.

*Venation color.*—Upper surface and lower surface: Can be either RHS 139A (Green) or RHS 155A (White), depending on the location of the stripes.

*Ligule* (*fringe of hairs*).—Color: RHS 139A (Dark-green) stripes with RHS 155A (White) stripes. Length: Very short, less than 0.1 cm.

Inflorescence description:

*General description.*—In mid-to-late summer, small terminal airy panicles appear between the leaves, the cultivar does not produce viable seed. In the fall the flower stalks turn orange or bronze.

*Lastingness of inflorescence on the plant.*—Each panicle blooms for 2-3 weeks, panicle is persistent. The species dies back to the ground in the winter, so foliage and inflorescence both die back to the ground.

*Fragrance.*—Absent.

*Panicle.*—Quantity: One panicle (culm) per stem. Length: 9 cm. Width: 3 cm.

*Rachis.*—Length: Up to 4 cm, continuous with culm. Width: 0.08 cm. Aspect: Rachilla emerging at about 33 degree angle to main branch. Color: RHS 11A (Yellow).

*Spikelet bud.*—Length: 0.6 cm. Width: 0.1 cm. Shape: Narrow, lanceolate. Color: Glumes are RHS 185D (Greyed-purple), florets are RHS 145C (Yellow-green).

*Spikelet.*—General: A single floret enclosed by one glume and one lemma, glume. Quantity (per panicle): 12 spikelet buds per panicle, 3 to 4 florets per spikelet (or 48 spikelets per panicle). Shape: Lanceolate. Surface texture: Glabrous. Apex: Acute. Base: Cuneate. Margin: Entire. Length: 0.4 cm. Width: 0.05 cm. Color: RHS 145C with RHS 185D at the tip.

*Lemma.*—Shape: Lanceolate. Surface texture: Glabrous. Apex: Acute. Base: Cuneate. Margin: Entire. Length: 0.3 cm. Width: 0.05 cm.

Reproductive organs:

*Stamens.*—Quantity: 2. Shape: X-shaped. Anther: Dorsifixed. Color: RHS 185D. Pollen: Amount: Sparse. Color: RHS 162A.

*Pistils.*—Quantity: 2. Shape: Fimbriate. Length: 0.04 cm. Color: RHS 145C. Ovary color: RHS 145C.

Fruit and seed set: No seed set observed.

Disease and insect resistance: The species has almost no insect or disease problems, as observed and is not favored by deer.

COMPARISON WITH PARENTAL AND COMMERCIAL VARIETYS

'Fubuki' differs from the parent 'Aureola' (unpatented) in that 'Fubuki' has white and green striped foliage, while 'Aureola' has gold and green striped foliage. Additionally, 'Fubuki' has a more compact growth habit that 'Aureola'.

'Fubuki' differs from the commercial comparison variety 'Nicolas' (U.S. Plant Pat. No. 19,898) in that 'Fubuki' has white and green striped foliage, while 'Nicolas' has green to yellow-green non-striped foliage.

I claim:

1. A new and distinct variety of *Hakonechloa* plant as shown and described herein.

* * * * *